United States Patent [19]  [11] Patent Number: 4,845,795
Crawford et al.  [45] Date of Patent: Jul. 11, 1989

[54] AUTOMATIC CLEANING DEVICE

[75] Inventors: Alan D. Crawford, Burbank; Allan B. Johnson, Tarzana, both of Calif.; John M. Trenary, Fort Collins, Colo.

[73] Assignee: Dental Research Corporation, Tucker, Ga.

[21] Appl. No.: 265,311

[22] Filed: Oct. 25, 1988

Related U.S. Application Data

[63] Continuation of Ser. No. 170,674, Mar. 16, 1988, abandoned, which is a continuation of Ser. No. 743,100, Jun. 10, 1985, abandoned.

[51] Int. Cl.$^4$ ............................................. A46B 13/02
[52] U.S. Cl. ..................................... 15/22 R; 15/28; 74/30
[58] Field of Search ................ 15/22 R, 22 C, 28, 29, 15/21 R, 77; 128/62 R, 62 A, 49; 74/30

[56] References Cited

U.S. PATENT DOCUMENTS

| | | |
|---|---|---|
| 216,537 | 6/1879 | Skinner . |
| 947,908 | 2/1910 | Heglar . |
| 1,498,215 | 6/1924 | Vidaver . |
| 1,947,324 | 2/1934 | Zerbee . |
| 2,044,863 | 6/1936 | Sticht . |
| 2,215,031 | 9/1940 | Elmore . |
| 2,476,154 | 7/1949 | Lohs . |
| 2,598,275 | 5/1952 | Lakin . |
| 2,668,968 | 2/1954 | Dobrowolski . |
| 2,843,706 | 7/1958 | Oppel . |
| 2,891,360 | 6/1959 | Duffie . |
| 3,029,451 | 4/1962 | Barr . |
| 3,104,405 | 9/1963 | Perrinjaquet . |
| 3,143,697 | 8/1964 | Springer . |
| 3,144,178 | 8/1964 | Sarnoff . |
| 3,281,878 | 11/1966 | Meza Roiz . |
| 3,510,747 | 5/1970 | Petrides . |
| 3,864,779 | 2/1975 | Thomas . |
| 3,925,841 | 12/1975 | Caliendo . |
| 3,994,039 | 11/1976 | Hadary . |
| 4,079,517 | 3/1978 | Zacharia . |
| 4,156,620 | 5/1979 | Clemens ............................. 15/22 R |
| 4,274,173 | 6/1981 | Cohen . |
| 4,326,314 | 4/1982 | Moret et al. . |
| 4,346,492 | 8/1982 | Solow . |
| 4,374,354 | 2/1983 | Petrovic et al. . |
| 4,418,633 | 12/1983 | Krautkremer et al. . |
| 4,545,087 | 10/1985 | Nahum . |

FOREIGN PATENT DOCUMENTS

| | | |
|---|---|---|
| 996319 | 9/1976 | Canada . |
| 357041 | 8/1922 | Fed. Rep. of Germany . |
| 1160821 | 1/1964 | Fed. Rep. of Germany . |
| 2201745 | 10/1972 | Fed. Rep. of Germany . |
| 2825179 | 12/1979 | Fed. Rep. of Germany . |
| 784709 | 7/1935 | France . |
| 2368854 | 10/1976 | France . |
| 2418636 | 9/1979 | France . |
| 452961 | 9/1936 | United Kingdom . |
| 500517 | 2/1939 | United Kingdom . |
| 985533 | 3/1965 | United Kingdom . |
| 1208149 | 10/1970 | United Kingdom . |
| 1438372 | 6/1976 | United Kingdom . |
| 2139483 | 11/1984 | United Kingdom . |

OTHER PUBLICATIONS

PCT Publication No. WO-A/8400099.

Primary Examiner—Edward L. Roberts
Attorney, Agent, or Firm—Watts, Hoffmann, Fisher & Heinke Co.

[57] ABSTRACT

A periodontal cleaning device including a hollow housing having a handle member and a brush head member. The brush head includes a gear train reciprocally driven by a rack. The gear train includes at least one drive gear engageable by the rack which in turn drives a plurality of series interconnected driven gears. The drive gear includes one portion engaged by the rack and another portion engaged by an adjacent driven gear. An axial width of a gear portion of the drive gear is greater than the axial width of gear portions of the driven gears so that in operation, the rack does not engage the driven gears. The drive and driven gears each include a tuft holder by which bristles are removably held.

37 Claims, 10 Drawing Sheets

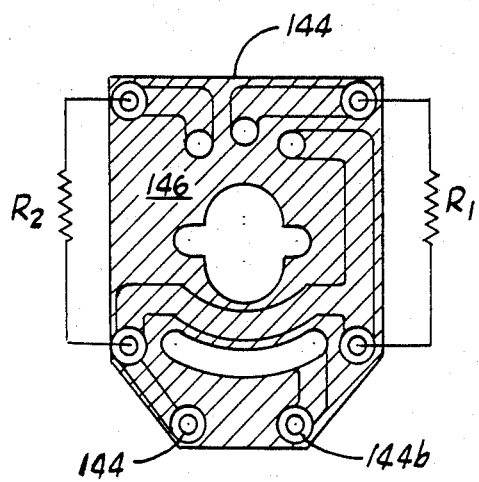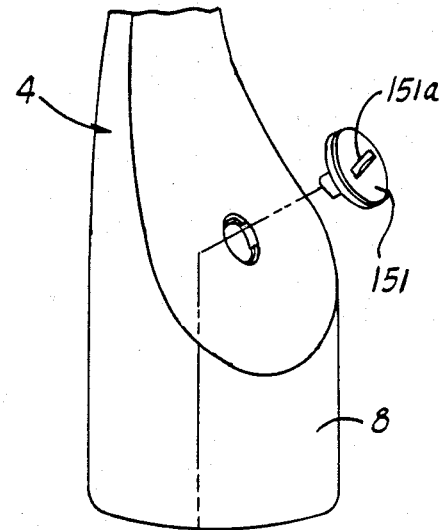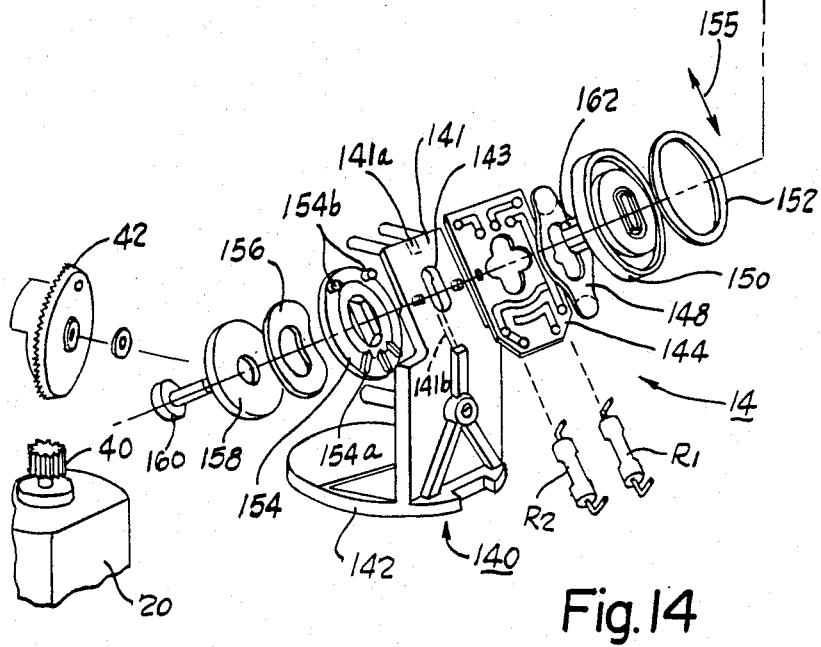
Fig. 14A
Fig. 14

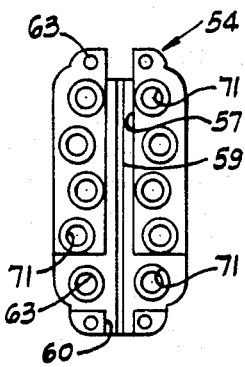
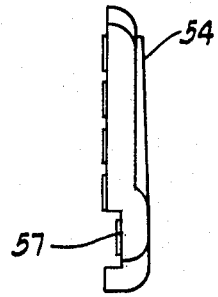
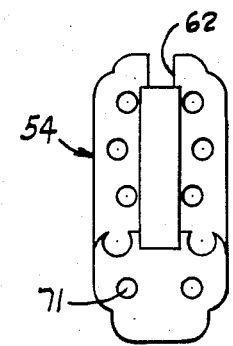
Fig. 23　　　Fig. 25　　　Fig. 26
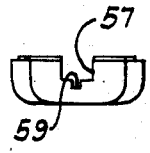
Fig. 24
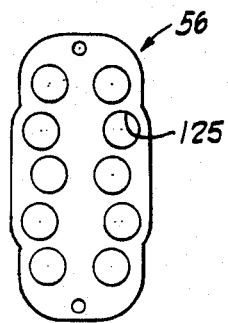
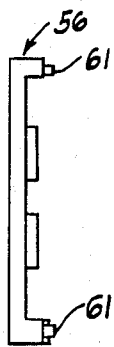
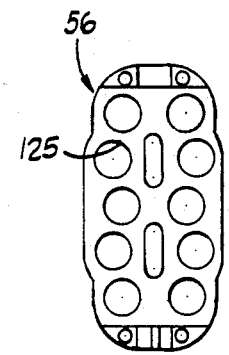
Fig. 27　　　Fig. 29　　　Fig. 30
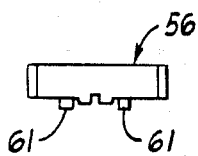
Fig. 28

AUTOMATIC CLEANING DEVICE

This is a continuation of co-pending application Ser. No. 170,674, filed on Mar. 16, 1988, now abandoned, which is a continuation of application Ser. No. 743,100, filed 6-10-85, now abandoned.

DESCRIPTION

TECHNICAL FIELD

This invention relates to the field of cleaning devices, and more particularly relates to a new and improved automatic cleaning device having improved electro-mechanical characteristics for cleaning, polishing, scrubbing or the like. In the preferred form illustrated, the device embodies a periodontal (e.g. tooth brush) device constructed and arranged to reduce oral debris, calculus formation, and periodontal disease.

Related Patents

The present invention constitutes a modification of applicant-assignees' prior U.S. Pat. No. 4,156,620 granted May 29, 1979. Such patent constitutes a continuation-in-part of Ser. No. 489,812, filed July 18, 1974, now abandoned.

BACKGROUND OF THE INVENTION

Heretofore, it has been known to provide various types of powered brush devices for cleaning, polishing, scrubbing or the like. Such devices have formal application, for example, in cleaning, polishing, and scrubbing items including cuticles, jewelry, housewares (e.g. utensils), teeth or the like wherein there is a need to treat small and/or relatively inexcessible surfaces which are curved as well as flat. In cleaning teeth for example, prior powered tooth brushes have included tufts and bristles moved in a rotary, arcuate, reciprocating, or orbital path by a power mechanism and on larger paths by hand movement. Another design includes powered brushes in which the brush head is substantially stationary and individual tufts are mechanically rotated along their own axis but unidirectionally. Such prior powered brushes, for example, are disclosed in U.S. Pat. No. 2,215,031 to N. Elmore wherein the individual tufts of the brush head continuously rotate in one direction. Because of this unidirectional rotation, the individual tufts of these bristles tend to "run-out" of the crevices between large surfaces of teeth. In the mouth, the interproximal crevices and irregularly shaped openings make it difficult to insert the tufts of the brush into the crevices at right angles due to the curvature of the dental arch. This tendency to move out of a crevice or indentation impairs the cleaning efficiency of the toothbrush because the tuft is difficult to position within a crevice for an amount of time adequate to achieve removal of foreign matter deposited within the crevice.

In applicant-assignees prior U.S. Pat. No. 4,156,620, the electric-toothbrush disclosed includes means for rotating at least one tuft about its central axis in a controlled reciprocating manner whereby adjacent tuft is rotated a predetermined number of turns in one direction and then rotated a predetermined number of turns in the opposite direction relative to an adjacent tuft.

More specifically and as disclosed in said prior patent, in a preferred embodiment of the invention there is provided a plurality of tufts of filaments, and each of the tufts is rotated about its own axis in a controlled and predetermined manner. In particular, each tuft is rotated in a controlled reciprocal fashion and immediately adjacent tufts are counter-rotated. The tufts are rotated about their central axis in a first direction from a generally neutral position of maximum projected length to a position of maximum filament twist so that the projected length of the tuft diminishes and the tuft is stiffened for effective power transmission, and the tufts are reciprocally rotated about their central axis from the position of maximum filament twist. The last step of reciprocal rotation moves the filaments in each reciprocating cycle from a position of maximum twist in a first direction and a minimum projected length to a position of maximum twist in a second direction in generally the same minimum projected length, and then back to a position of maximum twist in a first direction and a minimum projected length while three times passing through a general neutral position of maximum projected length. This matter produces a sweeping action as well as a "pumping" action to force the tuft filaments into a positive gripping the work surface whether it be curved or flat resulting in an effective cleaning thereof.

As in said prior patent and to enable confining of the tufts on the work surface or, for example, within the interproximal crevices for a period long enough to attain thorough cleaning, each individual tuft is reciprocally rotated. In a periodontal application, for example, this rotation is commenced in one angular direction for a distance sufficient to produce both effective energy transfer and lateral movement of the tuft across the interproximal crevice to clean both approximal (mesial and distal) surfaces, but less than the amount which would give rise to "run-out" of the tuft and expulsion from the interproximal crevice. Then each tuft is rotated in the opposite angular direction, again just far enough to produce the same cleaning results with effective energy transfer while avoiding expulsion of the tuft from the work surface whether it be flat or curved, such as in an interproximal tooth crevice.

In the periodontal application of said prior patent, and in addition to the mesial and distal surfaces noted above, each tooth has a facial and a lingual surface, all four of which define the vertical surfaces of a tooth crown. Because the gingival margins of the interproximal crevices, usually defined by the interdental papilla, and the gingival margins of the raised facial and lingual tooth surfaces between the approximal surfaces are vertically staggered, the tufts are also preferably arranged in a staggered relationship in each row of tufts. A first set of long tufts may be positioned along a first line in the brush head and a second set of shorter tufts may be positioned along a second line in the brush head generally parallel to and spaced from the first line. Within this staggered arrangement, the long tufts reach into interproximal crevices of the teeth, and the shorter tufts clean the raised face areas of the teeth near the gingival.

Another desirable characteristic of the applicant-assignees prior patented brush is that there is reduced vibratory movement of the brush head itself. Therefore, the brush head can be moved slowly and gently over the tooth surfaces and adjacent gingiva. The entire head of the brush does not oscillate, rotate, move in circular or elliptical paths, or become involved in any movement other than that imparted by the user. This characteristic is particularly important in cleaning teeth because the amount of cleaning motion that can be imparted to a moving brush head cannot be large enough to cause so-called "cheek shake" by action of the brush head in moving against the inner surfaces of the cheek.

In the dental field and for reference to prior manual and/or electric toothbrush devices, attention is brought to the following patents:

| U.S. Patent Documents | |
|---|---|
| 793,587 | 2,682,066 |
| 1,476,433 | 2,799,878 |
| 1,557,244 | 3,103,679 |
| 1,712,579 | 3,178,754 |
| 2,140,307 | 3,242,516 |
| 2,215,031 | 3,400,417 |
| 2,598,275 | 3,577,579 |

| Foreign Patent Documents | |
|---|---|
| 634,607, Germany, 8/1936 | 2,263,432, Germany, 5/1974 |
| 1,114,464, Germany 10/1959 | 480,510, Italy, 3/1954 |
| 2,215,799, Germany 10/1972 | 1,081,021, United Kingdom, 8/1967 |

Other patents and/or publications known to applicant will be made of record under applicants' Prior Art Disclosure Statement.

Accordingly, though prior automatic-type toothbrushes have been referred to by way of example, it is to be understood that these and other related problems in the cleaning of teeth also may be present in other cleaning, polishing, scrubbing or like applications. Such may be case with workpieces, such as cuticles, jewelry, housewares, or the like, particularly in cleaning applications where brush accessibility and/or brush "run-out" is a problem.

SUMMARY OF THE INVENTION

The present invention constitutes an improved modification of the application-assignees aforementioned U.S. Pat. No. 4,156,620 and may be adapted for use in other cleaning, polishing, scrubbing and the like applications, in addition to being usable, in a preferred form, as a periodontal device.

Accordingly, in the present invention there is provided a new and improved cleaning device which is of a portable, light-weight yet rugged construction, and which is significantly compact in size for facile handling particularly in relatively inaccessible areas, such as might be presented in cleaning cuticles, jewelry pieces, and the like, as well as cleaning tooth surfaces.

Another object of the present invention is to provide a motor driven cleaning device having an improved power train assembly including a compact rack and pinion driven means constructed and arranged for smooth power and torque transmission with reduced mis-alignment and wear between the component parts.

A further object of the present invention is to provide a motor driven cleaning device which has an improved rack and pinion assembly including a reciprocable rack disposed for substantially simultaneously rotating a plurality of tuft holding driven gear means via tuft holding drive gear means, and with said rack remaining in substantial contact with said drive gear means during operation thereof.

A yet further object of the present invention is to provide a motor driven cleaning device having an improved power drive train assembly including rack and pinion means actuatable within a compact brush head, and having a top and bottom bearing members with tuft holding drive gear means journaled in said bearing members for substantially simultaneously rotating a plurality of tuft holding driven gear members journaled in said bearing members upon reciprocal motion of said rack means.

A still further object of the present invention is to provide a motor driven cleaning device of the type characterized including two oppositely oriented rows of driven gear means including tuft holding driven gear members and tuft holding drive gear members adapted to be substantially simultaneously rotated upon reciprocation of a rack member disposed therebetween, and said rack member engaging only the bottom portions of said drive gear members with said rack member including cam-like guide means for controlling alignment of said rack member relative to said drive gears.

Yet another object of the present invention is to provide an improved motor driven, cleaning device of the character described wherein said driven gear members are disposed in piggy-back relation relative to said drive gear members with said driven gear members being substantially simultaneously rotated about their vertical axes without contact by said rack member upon engagement of said rack member with said drive gear members, and with said drive and driven gear members being arranged in a staggered relationship to effectively clean, for example, interproximal tooth crevices of the like.

Another object of the present invention is to provide a motor driven cleaning device of the character described wherein the improved drive train includes a drive rack which maintains constant contact with the drive gears, and which drive train allows selective orientation of the driven gears to provide a compact design which can be mounted in a relatively small brush head.

A still further object of the present invention is to provide a motor driven cleaning device of the character described wherein the drive and driven gear members include integral tuft holding receptical portions adapted to detachably retain therein tufts (filament bundles), and with said tufts being adapted to be detachably and interchangeably loaded into and out of said tuft receptacles for facile replacement and/or cleaning thereof.

A still further object of the present invention is to provide an improved motor driven cleaning device of the character described wherein the plurality of tufts are rotated in a controlled reciprocating manner whereby the tufts are subjected to a cyclical twisting action to alternately form right and left-handed helices, and with such twisting action providing a pumping and sweeping effect against the surfaces to be cleaned, thereby acting to draw the tufts into a gripping and tracking-like action with such surfaces and to reduce "run-out" with respect thereto.

An additional object of the present invention is to provide an improved motor driven cleaning device of the character described that may be battery-operated including a positive and simple multiple speed control switch assembly disposed in a power handle for selectively controlling reciprocation of the rack means and hence, counter-rotation of said tufts about their vertical axes.

A still further object of the present invention is to provide an improved motor driven cleaning device of the character described having an improved housing for the battery-operated power supply and control switch assembly and which housing includes a power handle portion and a brush head portion with said housing including alternate means adapted for expelling and/or flushing cleansing media (e.g. toothpaste, water and the like) from around the drive train assembly.

Another object of the present invention is to provide such a cleaning device wherein the alternate expelling means includes, in one form, a pneumatic system which provides one automatic pumping action for expelling residue from the brush head, and another automatic pumping action which flushes a liquid cleaning media through the brush head.

A further object of the invention is to provide such a cleaning device which includes, in combination, a new re-charger support stand which is configured to provide multiple support positions for the device and to allow constant draining of residue materials therefrom.

Yet another object of the present invention is to provide such a cleaning device which includes, in combination, a tuft filling or re-loading kit which coacts with the brush head for filling or reloading tufts in the head.

An additional object of the present invention is to provide a cleaning brush of the character described which includes a novel dual tuft holder and drive and/or driven gear construction, and which tuft holder detachably mounts a tuft of polymeric filaments therein with the tuft filaments being heat-fused together at one end to provide a general solid, mass-like base portion for insertion and retaining engagement within the tuft holder.

The features of the present invention which are believed to be novel are set forth with particularity in the appended claim. The organization and manner of operation of the invention, together with further objects and advantages thereof, may best be understood by reference to the following descriptions taken in conjunction with the accompanying drawings, in the several figures of which like reference numerals identify like elements throughout.

BRIEF DESCRIPTION OF THE DRAWINGS

FIG. 14 is a generally exploded, perspective view illustrating the component parts of the control switch assembly of the present invention;

FIG. 14A is an elevational view of a printed circuit board of the type which may be used in accordance with the present invention;

FIGS. 23, 24, 25 and 26 are top, end side and bottom view, respectively, of the bottom bearing member in accordance with the invention; and FIGS. 27, 28, 29 and 30 are top, end side and bottom views respectively, of the top bearing plate in accordance with the invention.

BEST MODE FOR CARRYING OUT THE INVENTION

Figure 1:
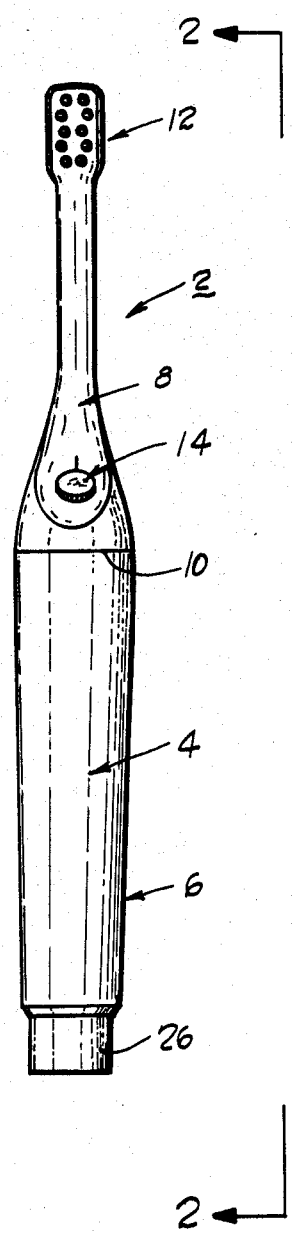
FIG. 1 is a front elevation view of the automatic cleaning device of the present invention.
Figure 2:
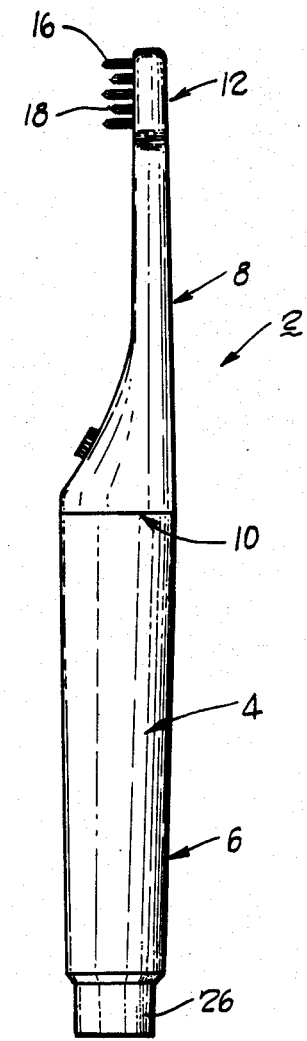
FIG. 2 is a side elevation view taken along the line 2—2 of the cleaning device illustrated in FIG. 1.

Referring now again to the drawings, and more particularly to FIGS. 1 and 2 thereof, there is illustrated the automatic cleaning device, designated generally at 2, of the invention, and which is adapted for use as a portable hand, held-device for cleaning, polishing, scrubbing or the like.

Though such device may be used for other various cleaning applications, it has been found to be particularly effective as a motor driven, tooth brush for removing debris and plaque from exposed tooth surfaces. Such cleaning application is disclosed in applicant-assignees prior U.S. Pat. No. 4,156,620, the disclosure of which is specifically incorporated herein by reference.

In the embodiment shown, the cleaning device 2 is illustrated for particular application as a motor driven tooth brush, and includes a hollow housing, as at 4, having a handle member 6 with a male re-charger portion 26, and a brush head member 8 which may be attached together in sealed relation via a washer seal, as at 10. At one end the brush head member 8 includes an integral brush head portion 12, and at the other end a switch assembly, designated generally at 14. The brush head portion 12 further includes a plurality of tufts 16 and 18 which are reciprocably, counter-rotated by the new and improved drive train assembly, as will hereinafter be more fully described.

In the embodiment illustrated, the tufts are preferably made from a polymeric material, such as nylon, and include a series of longer 16 and shorter 18 tufts which may be disposed, in two rows (FIG. 1) with there being, for example, six long tufts and four short tufts. These long and short tufts are preferably disposed in a staggered orientation along the brush head portion 12 to provide improved cleaning in periodical use, for example, of the interproximal tooth crevices, as disclosed in aforementioned U.S. Pat. No. 4,156,620.

Figure 4:
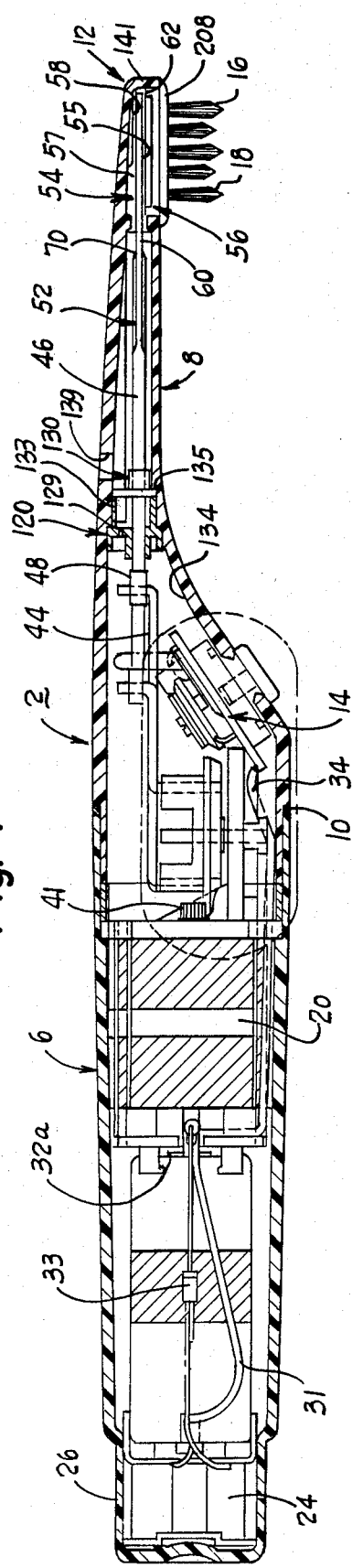
FIG. 4 is horizontal cross-sectional view of the automatic cleaning device illustrated in FIG. 3.
Figure 3:
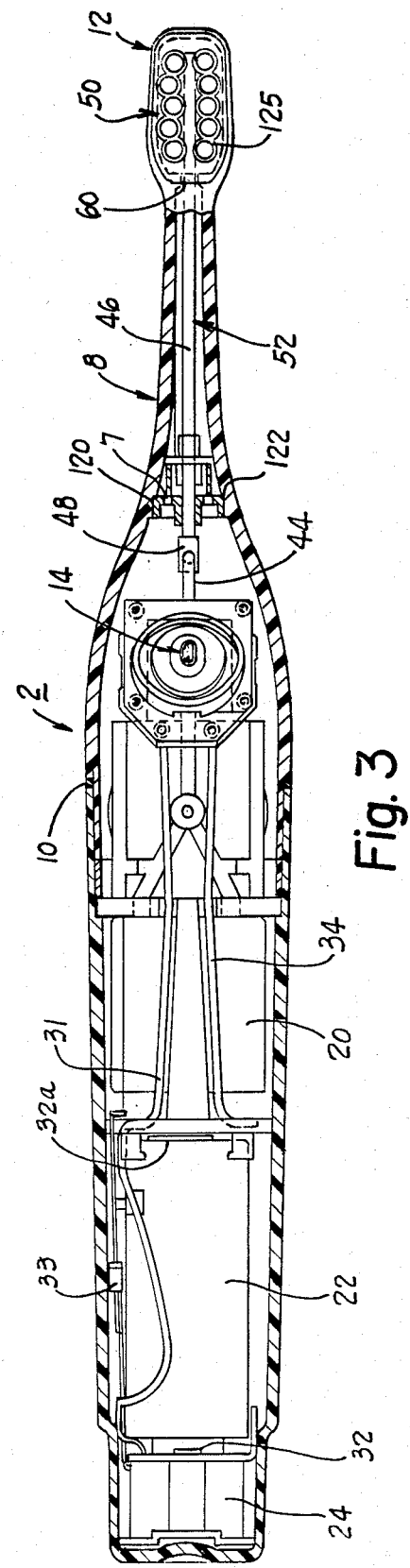
FIG. 3 is a vertical cross-section view of the automatic cleaning device illustrated in FIGS. 1 and 2.
Figure 17:
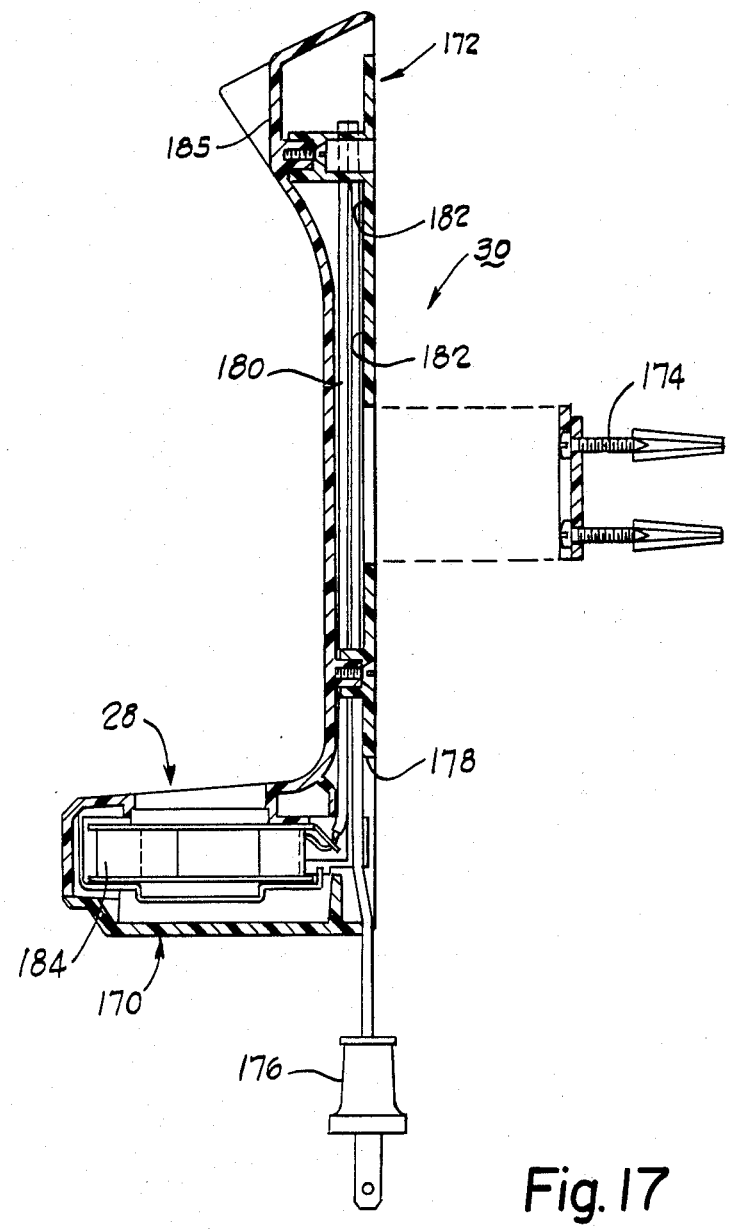
FIG. 17 is a general horizontal section view illustrating a charger stand assembly for use in storing and/or re-charging the battery-powered cleaning device in accordance with the present invention.

As best illustrated in FIGS. 3 and 4, a drive motor 20 is powered by a battery pack 22, which may be of the nickel cadmium type for ready charging via a secondary voltage coil 24 incapsulated in an integral male socket portion 26 of the handle portion 6. This socket portion 26 is detachably received in a corresponding female socket portion, as at 28 in FIG. 17, provided in a charger base assembly 30 having a primary charging coil. An electrical circuit is defined with one side of the secondary coil 24 attached to a negative battery terminal connector 32 (FIG. 4). The other side of the secondary coil 24 is coupled through a diode 33 to the positive battery terminal 32a. The diode rectifies voltage outputs from the coil 24.

A second electrical circuit includes the battery 22, motor 20 and switch 14. The negative battery terminal 32 is coupled to the switch 14 by a conductor 31. This switch 14 selectively energizes the motor 20 by coupling the battery 22 across the motor. A conductor 34 completes the circuit by connecting the switch to the motor 20. An opposite side of the motor is connected to the positive battery terminal.

In the present invention, a transmission is energized by the power source and includes a pinion gear 40 (FIG. 3) operatively associated with the output shaft 41 (FIG. 14) of the motor 20. The pinion gear 40 drives a crown or face gear 42 (FIGS. 3 and 4) which is rotatably mounted within the handle portion 6 such that when the motor 20 is energized, rotation of the pinion 40 causes rotation of the face gear 42 about a vertical axis which is generally normal to the longitudinal central axis of the housing 4.

Figure 5:
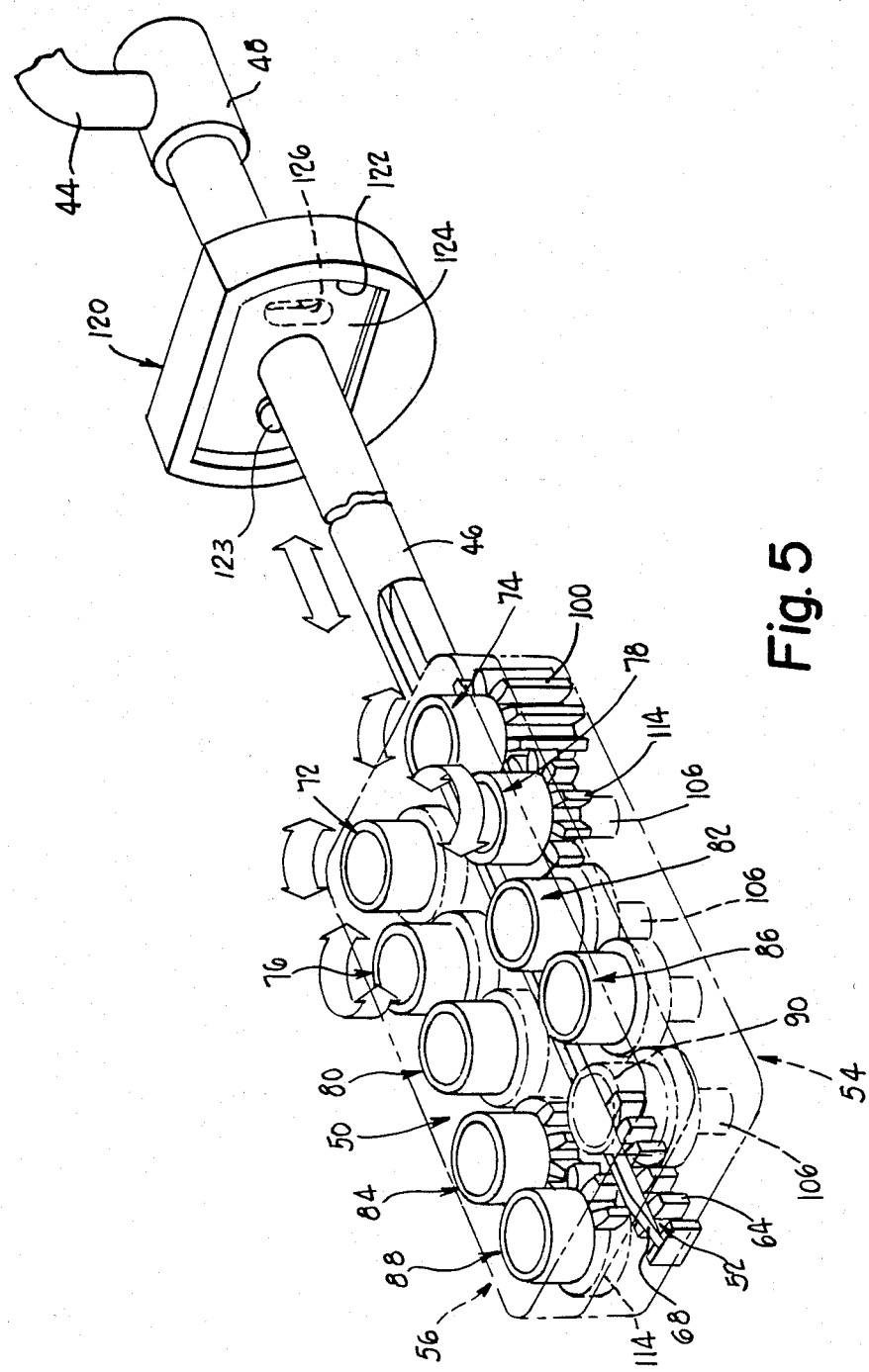
FIG. 5 is a partially-exploded, perspective view of the automatic cleaning device of the present invention particularly illustrating the drive train assembly thereof.

As best illustrated in FIGS. 4 and 5, a crank arm or rod 44 is pivotly connected to a rack drive shaft 46 by means of a swivel member 48. By this arrangement, the drive train assembly, designated generally at 50, (FIGS. 3, 4 and 5) transmits the mechanical energy via the power transmission to the series of tufts 16 and 18 in a controlled, reciprocating manner so that the rotation of the tufts is reversed after a predetermined number of revolutions. Also, the tufts are counterrotated, that is, adjacent tufts rotate in opposite directions relative to one another, as illustrated by the arrows in FIG. 5.

More specifically, the rotational movement of the crown or face gear 42 is transferred into linear reciprocating motion via the drive train assembly 50 (FIG. 5) for counter-rotating the tufts 16 and 18 about their vertical axes. For this purpose, one end of the crank arm 44 is operatively connected to one end of the face gear 42 which connection is radially displaced from the central axis of the face gear and the rack drive shaft 46. This connection, via the swivel 48, acts such that the drive shaft 46 will be caused to move in linearly reciprocating cycles (dotted line) along its longitudinal axis when the motor unit 20 (FIG. 4) is energized. This reciprocating motion results from the action of the crank arm 44 moving in a circular path defined by movement of the face gear 42. The length of stroke defined in reciprocating movement of the rack drive shaft 46 is a function of the radial distance between the center of the face gear 42 and the central point of attachment of the crank arm 44 to the face gear, as disclosed in aforementioned U.S. Pat. No. 4,156,620. Preferably, this stroke, for periodontal applications, is approximately 0.7 inches.

Now in accordance with an important aspect of the present invention, the drive train assembly 50 includes an elongated rack member 52 which may be made integral with the rack drive shaft 46 for reciprocal movement between top 54 and bottom 56 bearing members (FIG. 5 being reversed from FIG. 4 for purpose of clarity) which are preferably made from a polymeric material having good strength and wear characteristics. As best seen in FIGS. 3, 4, 18 and 19 the rack member 52 extends through a cavity, as at 58, defined between the confronting faces of the bearing members 54 and 56. An access opening, as at 60, may be provided on the rearward end between the bearing members 54, 56 to slidably receive the rack member 52. The opposite ends of the bearing member provide an access opening, as at 62, to enable the terminal end of the rack member 52 to extend slightly beyond the bearing members 54 and 56 during the maximum stroke thereof, as desired. The bearing members 54 and 56 may be detachably connected together by means of integral pins 61 received in pin holes 63.

The rack member 52 is of an elongated, unitary construction, including a plurality of oppositely disposed and laterally spaced rack teeth 64, which are disposed in the same generally horizontal plane. The rack member 52 includes integral, cam-like guide portions 66 which extend laterally outward therefrom and generally normal to the rack teeth 64. These guide portions 66 have inclined surfaces as at 68, at each of the forward ends (FIG. 5) so as to facilitate insertion into and out of the access opening 60 (FIGS. 3 and 4) provided between said bearing members 54 and 56. As best illustrated in FIG. 3, the rearward end of the rack member 52 has inclined shoulders, as at 70, which provide a stop for limiting forward axial reciprocal movement of said rack member, as desired.

Figure 6:
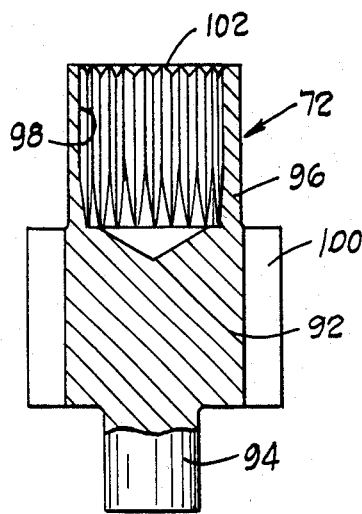
FIG. 6 is a vertical section view taken along the line 6—6 of FIG. 7, on an enlarged scale, illustrating one of the tuft holder drive gear members of the present invention.
Figure 8:
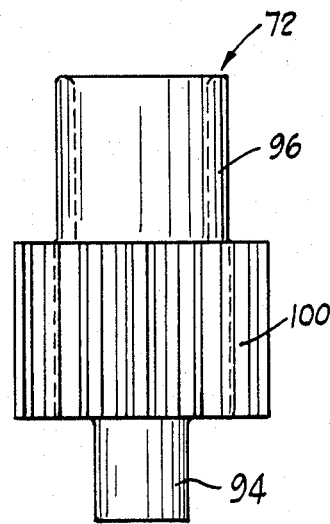
FIG. 8 is a front elevation view of the tuft holder drive gear member illustrated in FIG. 6.
Figure 7:
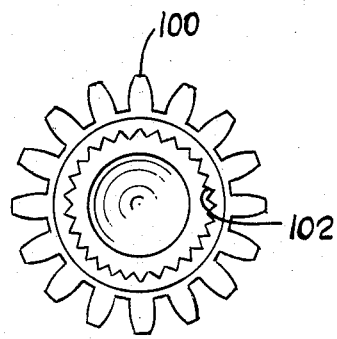
FIG. 7 is a top plan view of the tuft holder drive gear member illustrated in FIG. 6.
Figure 9:
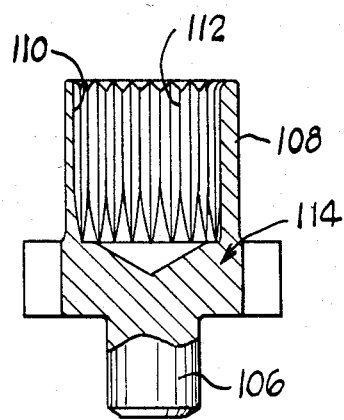
FIG. 9 is a vertical section view taken along the line 9—9 of FIG. 10, on an enlarged scale, illustrating one of the tuft holder driven gear members of the present invention.
Figure 11:
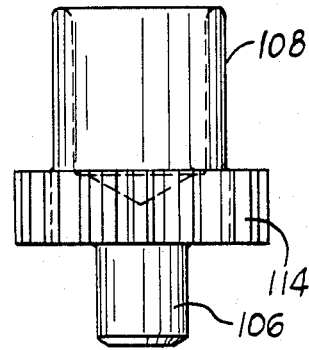
FIG. 11 is a front elevation view of tuft holder driven gear member illustrated inn FIG. 9.
Figure 10:
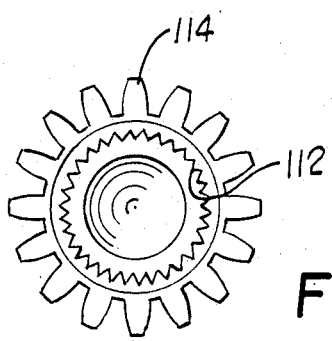
FIG. 10 is a top plan view of the tuft holder driven gear member illustrated in FIG. 9.

Now in accordance with the invention, the rack member 52 engages an oppositely disposed pair of tuft holder drive members 72 and 74 which, in turn, drive a series of tuft holder driven gear members generally designated at 72, 74, 76, 78, 80, 82, 84, 86, 88 and 90, respectively. The tuft holder drive gear members 72 and 74 are of identical construction and best illustrated in FIGS. 6, 7 and 8. As shown, each tuft holder drive member, as at 72, includes an elongated cylindrical body 92 having an integral, solid journal end portion 94 adapted to be journaled within a bearing opening 71 (FIGS. 23 and 26) provided in the top bearing member 54, and an integral receptacle-like portion 96 defining a cup-like recess for slidably receiving in press-fit relation therein, the tufts 16, 18. Disposed generally intermediate the end -portions 94 and 96 is an integral series of drive gear teeth, as at 100, for driving engagement with the driven gears, as will be described hereinafter. Preferably, the interior of the receptacle portion 96 may be axially serrated, as at 102, to enhance the frictional engagement for retaining the respective tufts therein.

As best illustrated in FIGS. 3, 13, 23 and 26, the bearing members 54, 56 provide mating halves which define a cavity, as at 55, therebetween. This cavity houses the drive train 50 and slidably receives there through the rack member 52. The bearing members 54, 56 together define at one end a generally inverted T-shaped recessed portion 60 adapted to slidably receive there though the corresponding guide portions 66 on the rack member 52. The top bearing member 54 has a recessed slot and groove extending axially therethrough, as at 57 and 59, which provide cam-like track for the upper guide portions 66 on the rack member 52. By this arrangement the rack member 52 is guided into and through the recessed slot 57 in the cavity 55 between the bearing members so as to maintain alignment and registration with the respective drive and driven gears of the gear train. Also, it will be seen that the upper or top bearing member 54 (FIGS. 3 and 13) has an enlarged boss portion 57 to receive the approximate upper one-half of the tuft holder drive gears 72 and 74, as will hereinafter be described.

The bearing members are preferably made from a polymeric material having good strength and wear characteristics. These members may be detachably connected together via integral pins 61 and pin hole openings 63 (FIGS. 24, 25, 26 and 27) to provide an efficient snap-action between the component parts for ready assembly or disassembly for inspection, cleaning and/or removal of the drive train components.

The respective tuft holder driven gear members, as at 76, are also of an identical construction and generally similar to the tuft holder drive gear members. These each include a body having an integral journaled portion 106, and an integral receptacle portion 108 defining a cup-like recess opening 110 having axial serrations 112 therein, as aforesaid. In this case, however, the driven gear members have integral driven gear teeth, as at 114, which are fore-shortened in axial width relative to the corresponding axial width of the drive gear teeth 100 of the drive gear members. Preferably, the axial width (e.g. 0.120 inches) of the gear teeth 100 on the drive gear members is approximately twice the corresponding axial width (e.g. 0.050 inches) of the gear teeth 114 on the driven gear members. By this construction and arrangement, the teeth 64 of the rack member 52 engage the approximate top one-half portion of the drive teeth 100 on the drive gearmembers 72 and 74 and hence, do not engage the down-stream driven gear members 76-90. The approximate lower one-half portion of the drive gears 100 of the drive gear members 72 and 74 then substantially simultaneously mesh with the first adjacent pair 76 and 78 of the driven gear members which then, in turn, drive, in piggy-back relation, the next successive driven gear members 80-90.

Accordingly, by this arrangement it will be seen that substantially all the torque load forces imparted by reciprocal movement of the rack member 52 are borne only by the gear teeth 100 on the drive gear members 72 and 74 which constitute, in effect, the working end of the drive train assembly. Also, this drive train construction allows relative rotation of the down-stream, piggy-back driven gears as the train need only be driven by one or more drive gears merely with the rack member 52.

Figure 19:
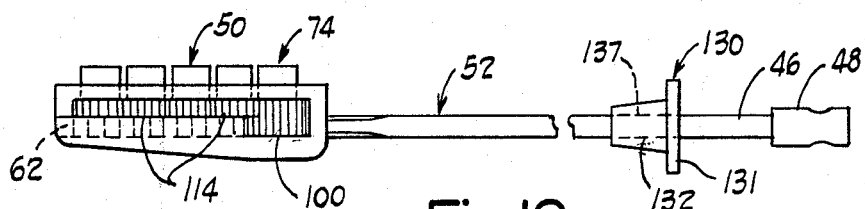
FIG. 19 is a side elevation view of FIG. 18.

In the invention, it is preferred that the axial width of the gear teeth 100 on the drive gear members and 74 be approximately twice the axial width of the driven teeth or such that the axial width of the driven gear teeth extends to approximately the mid-point (FIG. 13) of the drive teeth 100 on the driven gear members 72 and 74. Also, it is preferred that the transverse width of the rack teeth 64 be the same (e.g. 0.050 inches) the corresponding axial width of the driven gear teeth 114 but less than the corresponding axial length of the drive gear teeth 100 as best illustrated in FIG. 19. In a preferred form of the invention, there is hereinafter set forth a typical mechanical characteristics for the drive gears, driven gears, and drive rack:

| Drive Gears | |
|---|---|
| No. of Teeth | 14 |
| Diametral Pitch | 96 |
| Pitch Dia. (Theo.) | .14583 |
| Pressure Angle | 20° |
| Whole Depth | .0269 |
| Cir. Tooth Thickness | .0175/.0170 |
| Chordal Addendum | .0149 |
| Fin. Chordal Thickness | .0175/.0170 |
| Base Circle Dia. | .13704 |
| Center Distance | .1500 |
| No. of Teeth in Mate | 14/Rack |
| Face Width | .120 |

| Driven Gears | |
|---|---|
| No. of Teeth | 14 |
| Diametral Pitch | 96 |
| Pitch Dia. (Theo.) | .14583 |
| Pressure Angle | 20° |
| Whole Depth | .0269 |
| Cir. Tooth Thickness | .0175/.0170 |
| Chordal Addendum | .0149 |
| Fin. Chordal Thickness | .0175/.0170 |
| Base Circle Dia. | .13704 |
| Center Distance | .1500 |
| No. of Teeth in Mate | 14 |
| Face Width | .050 |

| Drive Rack | |
|---|---|
| No. of Teeth | 25 |
| Diametral Pitch | 96 |
| Pitch Plane | .0381 |
| Pressure Angle | 20° |
| Whole Depth | .0269 |
| Cir. Tooth Thickness | .0154/.0164 |
| Chordal Addendum | .0104 |
| Fin. Chordal Thickness | .0154/.0164 |
| Base Circle Dia. | — |
| No. of Teeth in Mate | 114 |
| Face Width | .050 |

Because of the controlled reciprocating linear movement of the drive rack member 52, each tuft 16 or 18 is rotated in a controlled reciprocating manner for a predetermined cycle. Reciprocating movement in one direction of one and one-half times the base circumference of each tuft is chosen in the preferred embodiment. By this arrangement, each tuft is rotated first one and one-half revolutions in one direction and then approximately one and one-half revolutions in the opposite direction. It is to be understood, however, that the amount of reciprocating rotation may vary in accordance with the diameter of the filaments in each tuft, the length and diameter of each tuft etc., as desired. The desirable speed for operation of the reciprocating rack 52 for periodontal applications, for example, may be approximately 1,500 cycles per minute with one and one-half revolutions in each direction per cycle. In such case, the tufts rotate at approximately 4,500 effective revolutions per minute.

Figure 12:
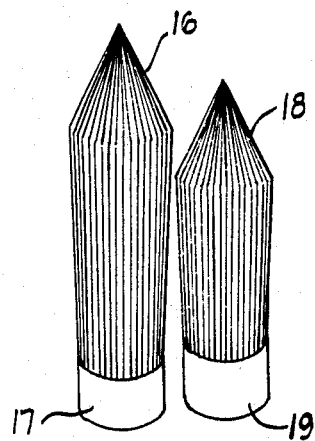
FIG. 12 is a generally perspective view of tuft units, on an enlarged scale, for detachable connection to the tuft holder receptacles of the present invention.
Figure 13:
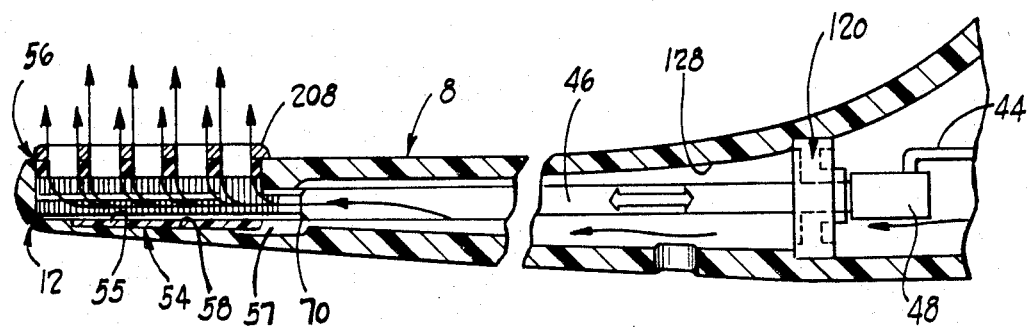
FIG. 13 is a fragmentary, partially-sectional view, illustrating one form of the expulsion system of the present invention.

As best illustrated in FIGS. 3, 4 and 12, the tufts 16 and 18 may be alternately arranged into staggered rows of long and short tufts. In a preferred form, the long tufts 16 in each row are indented or positioned closer to the longitudinal axis of the brush head portion 8 than the short tufts 18 in each row. Both the short and long tufts have tapered upper surfaces, defined by the tips of the filaments of each tuft. The tapered configuration of the tufts facilitates penetration into recessed cavities or interproximal crevices, in the case of dental applications. Each tuft is comprised of a plurality of filaments having a predetermined diameter and physical characteristics, so that the desired cleaning action will be realized with the rotational tuft movement of the present invention. For example, each tuft may have a diameter of approximately 0.090 inches and may contain hundreds of filaments, as desired.

As best seen in FIG. 12, the long and short tufts 16 and 18 are made from a polymeric material, such as nylon fused together at one end, as at 17 and 19, to provide a generally solid, mass-like base portion. This portion may be press-fit, for example, into the respective receptacle portions, as at 96 and 108, of the respective drive and driven gear tuft holder members 72–90 to facilitate insertion and registration of the tufts within the corresponding tuft holder receptacle.

Now in accordance with one embodiment of the invention, there is provided the pneumatic system for cleansing via a pumping action residue materials, such as tooth paste or the like, from the brush head portion 12 and particularly from the drive train 50. In this embodiment, the system includes a bearing drive member 120 which is preferably made from a polymeric material and which is fixably attached to the interior of the housing 4, as best illustrated in FIGS. 3, 4 and 5. This bearing member 120, receives therethrough the drive rack member 52 and provides a bearing support therefor. In the embodiment illustrated in FIG. 5, the bearing member 120 is provided with a recessed cavity, as at 122, which fixably mounts a flexible flapper valve member 124. The valve member is preferably made from a polymeric material, such as MYLAR TM, a trademark material of the DuPont Company. The flapper valve 124 is fixably attached to the bearing member 120 by means of a suitable fastener, as at 123 and has an aperture, as at 126, to enable ingress and egress of pneumatic pressure (e.g. air) therethrough. Accordingly, upon the rearward stroke of the rack drive shaft 46 and hence, the rack member 52, the flapper valve member 124 opens so as to draw air into the interior of the housing, as at 128, of the brush head portion 8. Upon reverse movement of the drive rack shaft 46 the valve 124 closes. This provides a pumping action upon forward movement of the rack member 52 which acts to force air out of the cavities 58 and 128 through suitable openings provided through and/or around the tufts 16 and 18 a clearance space, as at 125 (FIG. 18), between the tuft holders and the confronting surface of the lower bearing member 56, as illustrated by the arrows in FIG. 13. This pumping action provides a positive pressure in the drive train cavity 58 so that any residue material, such as tooth paste or the like, is flushed-out after normal usage thereof.

Figure 18:
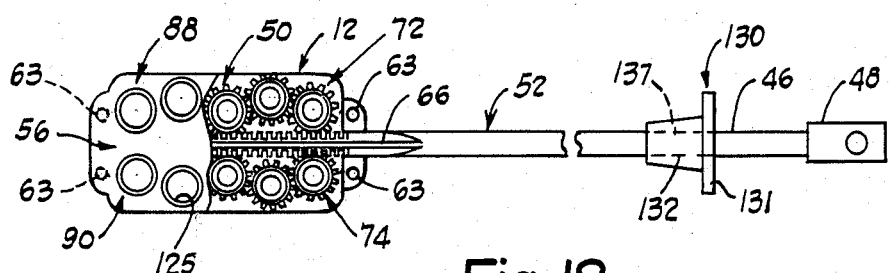
FIG. 18 is a fragmentary top plan view of the brush head on an enlarged scale relative to FIGS. 3 and 4.

In another embodiment, and best illustrated in FIGS. 3, 4, 18, and 19, the bearing member 120 is again fixably mounted internally of the housing 4 and in this form does not include the flexible flapper valve 124. Here a flexible seal member 130 having a base-like wiper portion 131 and an integral forward extending tapered conical portion 132 is fixably retained in the housing 4 against an integral elongated, hollow hub portion 133 of the bearing member 120. In this case, the base-like wiper portion 131 is frictionally retained against the confronting interior surface of the housing 4, as at 135, such that the drive shaft 46 is slidably passed through a passageway, as at 137, provided in the base 131 and conical portions 132 of the flexible seal, as seen in FIGS. 18 and 19. The base-like wiper portion 131 provides a friction, liquid seal against the confronting surface of the hub portion 133 so as to prevent the ingress of liquid behind the drive shaft 46 into the power handle of the device. As shown in FIG. 4, the bearing member 120 may have one or more apertures therein, as at 129, to prevent the formation of a vacuum behind the wiper seal 131 during reciprocal movement of the drive shaft 46. Also, in this embodiment the brush head portion 12 may be provided with outlet openings, as at 139, just forward of the wiper seal, and in the brush head portion, as at 139, to allow the ingress of a cleansing media, such as hot water or the like, therethrough. Accordingly, in this embodiment the liquid cleansing fluid may be poured into the openings 139 and moved axially through the brush head portion 12 via gravity and/or the pumping action of the drive shaft 46, and out through openings 141 for cleansing the drive train 50 within the brush head portion 12.

Now in the invention, and as best illustrated in FIGS. 3, 4, 14 and 14A, a new and novel control switch assembly 14 is detachably mounted on an interior wall surface 134 of the brush head portion 8 of the housing 4. As illustrated in FIG. 14, the components of the switch assembly 14 include a frame member 140 with an integral base portion 142. The frame includes an integral upper inclined support portion 141, having an aperture 143 extending therethrough and adapted to support a printed circuit board 144 thereon. This circuit board 144 contains a suitable contact switch circuit, as 146 (FIG. 14A, for actuation by a spring contact 148 retained by a switch body 150 via an O-ring seal 152. On the under side of the support portion 141 of the frame 140 is a detent 154 retained by a spring washer 56. This, in turn, is retained by a washer 158, retained by a screw 160, which may be threaded into a threaded collar 162 made integral with the switch body 150.

Figure 15:
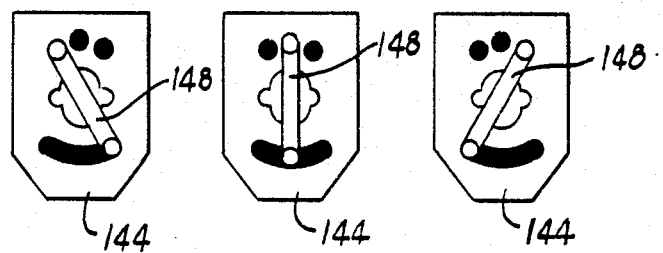
FIGS. 15 and 16 are generally schematic illustrations showing the various control positions of the control switch assembly according to the present invention.
Figure 16:
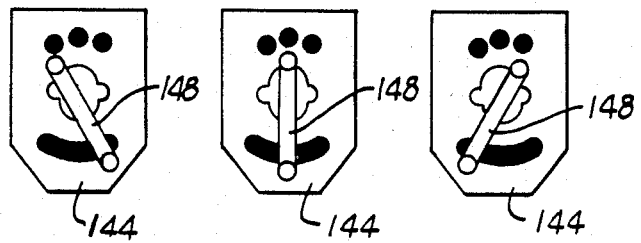

The switch contact 148 is slightly bowed away from the switch body 150. As the screw 160 is threaded into the collar 162, the combination of the spring washer 156 and the bowed configuration of the contact 148 bias the contact against the printed circuit board 144. Details of the print circuit board 144 are illustrated in FIGS. 15, 16 and 14A. The contact 148 is schematically illustrated in various positions selected by the user. In the three positions shown in FIG. 16, the motor 20 has been deactivated by opening the circuit between two circuit connections 144a, 144b.

Turning now to FIG. 15, contact positions for energizing the motor are illustrated. The user can rotate the switch body 150 by a button 151 that engages the body 150 through the housing. The button defines a slot 151a therein to facilitate rotation of the contact 148 to the three positions shown in FIG. 15. In the position shown to the right of FIG. 15, the configuration of the switch 14 couples the motor 20 directly across the battery. In the two other positions shown in FIG. 15, the switch 14 selectively adds one of the resistors R1, R2, into the motor circuit to reduce the motor speed. Representative values for the resistors R1, R2 are 0.1 and 0.22 ohms with the larger resistance R2 providing low speed motor operation. Details of the contact points on the printed circuit 144 are shown in FIG. 14A.

A detent action is provided by the detent 154 in combination with the incline support portion 141. A surface of the incline portion 141 facing the detent defines two ridges 141a, 141b shown in phantom in FIG. 14. A corresponding face of the detent 154 defines a series of grooves 154a that engage a bottom ridge 141b to lock the switch contact in one of the positions shown in FIGS. 15 and 16. When the motor is to be switched from high to medium speed, the user rotates the button 151 causing the ridge 141b to ride up over the groove into an adjoining groove and again lock the switch in place. By slidably moving the switch body 150 in the direction illustrated by the arrow 155 in FIG. 14, the motor can be turned on and off. The ridge 141a provides a detent action to the on and off motion of the switch by engaging an edge of the detent between two bosses 154b. The bosses 154b in the detent switch 154 limit rotation of the switch body so that in the event the user attempts to rotate the button 151 beyond either the high speed or low speed position, continued rotation is prevent by contact of these bosses 154b with the ridge 141a on the incline frame portion 141.

The novel construction of the switch and frame allow the user to adjust the motor speed in either an off or on position. The detent and motion limiting aspects of the switch assembly insure proper switch setting and prevent unintended movement of the switch during motor operation. The use of the frame as both a support for the switch and a mounting for the motor drive train contributes to a compact construction for the cleaning device 2.

Now in FIG. 17 there is illustrated a charger support stand assembly 30 which includes the aforementioned female socket 28 for receipt of the male socket portion 26 of the cleaning device for purpose of recharging the batteries 22 of the power supply. As shown, the charger assembly 30 is of a generally L-shaped configuration having a hollow base portion 170 and an integral upstanding, hollow back support portion 172 for detachable connection to a supporting wall or the like (not shown) via suitable fasteners, as at 174. The charger includes a conventional power cord 176, which may be inserted through an inlet opening 178 and wound around a bracket retainer 180 mounted within an interior cavity 182 formed in the back support 172. The base portion 170 includes a primary bobbin 184 for supporting a primary coil for energizing the secondary coil assembly 24 disposed in the handle portion 6 of the cleaning device, as illustrated in FIGS. 3 and 4.

The support stand 30 has a generally L-shaped configuration which enables multiple storage and/or use positions thereof. For example, the base portion 170 allows the stand to be freely mounted on a work surface, such as a counter or the like, and the back support portion 172 enables the stand to be hung, for example, on a support surface such as a wall or the like. Also, the stand is constructed and arranged such that the cleaning device can be placed in a draining mode for draining residue materials from the brush head member 9. Specifically, with the male socket portion 26 mounted in the female socket 28 of the base portion 170 of the stand and the brush head portion 12 mounted on a forward support surface of an integral head portion 185 of the stand, the housing 4 of the cleaning device 12 is inclined slightly downwardly from the rear to the front to provide constant drainage through the outlet opening 141 provided in the brush head portion 12.

Figure 20:
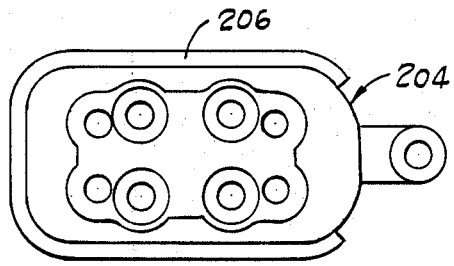
FIG. 20 is a bottom plan view of the filling or re-loading fixture of the present invention.
Figure 21:
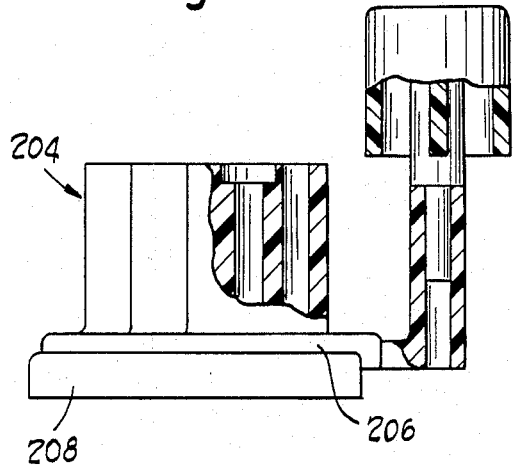
FIG. 21 is a side elevation view, partially in section, of the fixture of FIG. 20.
Figure 22:
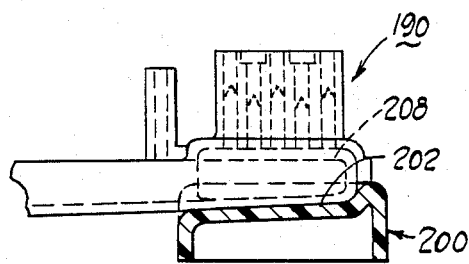
FIG. 22 is a fragmentary side elevation view, partially in section, illustrating the support base mounting the brush head during the filling or re-loading operation.

Now as best illustrated in FIGS. 20, 21 and 22, there is illustrated a new and novel filling or re-loading kit, designated generally at 190, for filling or re-loading the tufts filaments 16 and 18 into the respective tuft holder members of the associated drive and driven gears. As shown, the kit includes a base member 200 having a support recess 202 which is contoured to receive the confronting surface of the brush head portion 12. This base member provides a support for the brush head portion and acts to prevent sliding and/or rotational movement thereof during filling or re-loading of the tufts. A cap-like fixture member 204 is provided which has a bottom skirt-like portion 206 defined by an integral flange 208 which set over and around a corresponding cover member 208 mounted over and around the lower bearing member 54, illustrated in FIGS. 3 and 13. The cap member 204 includes an upper body portion 210 which has a plurality of generally symmetrically oriented, cylindrical passageways of a longer 212 and a shorter 214 construction for receiving the tufts 16 and 18 therein. The passageways are disposed in substantially parallel relationship with respect to one another and provide guides for inserting the tufts contained therein into the respective tuft holders of the associated drive and driven gear members. As illustrated, the sorter cylindrical passageways have a counter-sunk portion, as at 216, to receive a correspondingly shaped integral collar member 218 formed on a manual tamper member 220. The tamper member 220 includes an elongated, cylindrical tamper element 222 for tamping the respective tufts through the cylindrical passageways and into the tuft holders, as aforesaid. In one form, the tamper element may have a generally conical recessed cavity, as at 224, to receive the corresponding tapered end of the respective tuft or may simply have a generally flat configuration, for example, in the case of tufts which are trimmed flat. It will be understood that the cap member may have any array or number of cylindrical passageways to accommodate the various size and arrangement of the tufts to be utilized in accordance with the invention for a particular cleaning application.

As illustrated, a cap member may included an integral upstanding guide portion 226 which includes another cylindrical passageway 228 which extends parallel to the aforementioned passageways 212 and 214 for insertion and dispensing another single tuft therefrom. This guide portion also provides a handle for manually manipulating the cap member thereby to orient the axial passageways relative to the corresponding tuft holder receptacles. For example, in use the guide portion 226 can be used as a handle for registering the other cylindrical portions or the body 210 defining such cylindrical portions can be used as a handle for registering the single guide portion when it is desired to replace, for example, only one of the tufts relative to the desired tuft array. Accordingly, this kit provides upper and lower base and cap members which may be effectively utilized, in combination, with the cleaning device for filling or reloading tufts, of any configuration, orientation or size, into the associated tuft holders.

While a particular embodiment of the invention has been shown and described in reference to a periodontal cleaning device, it is to be understood that the principals involved with respect to the construction and function of such device can be effectively utilized in other cleaning, polishing, scrubbing or like applications where relatively small inaccessible parts having curved and or flat surfaces are to be cleaned. Accordingly, it will be seen that modifications may be made in the invention without departing from the spirit and scope of the appended claims.

We claim:

1. An automatic cleaning device for cleaning work surfaces comprising, a hollow housing having a handle member and a brush head member, said brush head member including drive train means disposed interiorly thereof, said drive train means including at least one tuft holding drive gear drivingly engaging a gear train including a plurality of series connected, tuft holding driven gears, said drive gear and driven gears rotated and counter rotated upon reciprocation of a power driven rack means, said rack means engaging only said tuft holding drive gear, said tuft holding driven gears being reciprocally rotated and counter-rotated by Baid tuft holding drive gear without substantial driving engagement by said rack means.

2. An automatic cleaning device in accordance with claim 1, wherein said tuft holding drive and driven gears each include a body member having a tuft receiving receptacle portion and an integral drive or driven gear portion, and the drive gear portion on said drive gear having a greater axial width as compared to the corresponding axial width of said driven gear portion on an associate<driven gear so that said rack means substantially meshes only with the drive gear portions of said drive gear and said driven gear portion's drivingly meshing with one another.

3. An automatic cleaning device in accordance with claim 1, wherein said rack means.includes an elongated rack member having a plurality of laterally space drive teeth on opposed sides thereof, and said rack member including guide means disposed generally intermediate said drive teeth for guiding reciprocal movement of said rack member relative to said tuft holding drive gear.

4. An automatic cleaning device in accordance with claim I, wherein said tuft holding drive and driven gears includes a drive or driven gear portion, the drive gear portions of said tuft holding drive gear being drivingly engaged by said rack means such that said tuft holding driven gears are reciprocally rotated and counter-rotated by meshing engagement with the drive gear portions of the tuft holding drive gears while being substantially free of driving engagement with rack means.

5. An automatic cleaning device in accordance with claim 1, wherein said tuft holding drive and driven gears each include a tuft holding receptacle portion and an integral drive or driven gear portion, and said receptacle portion adapted to detachably retain therein a tuft of filaments.

6. An automatic cleaning device in accordance with claim 5, wherein said tufts each comprise a bundle of polymeric filaments, said filaments in each tuft being fused together at one end to provide a generally solid, mass-like body for detachable insertion into and out of the associated of said receptacle portions.

7. An automatic cleaning device in accordance with claim 5, wherein said tufts are disposed in at least two oppositely disposed rows and on opposed sides of said rack means, the tufts in each of said rows being oriented in a generally staggered relationship relative to one another, and the adjacent tufts in each of said rows being longer and shorter, in axial length, relative to one another.

8. An automatic cleaning device in accordance with claim I, including top and bottom bearing members defining a cavity therebetween adapted to receive said tuft holding drive and driven gears therein, said tuft holding drive and driven gears each including integral drive and driven gear portions, respectively, and integral tuft holding receptacle portions, said drive and driven gears being rotatably journaled at one end in said top bearing member with said receptacle portions extending therethrough and communicating with the exterior of said bottom bearing member and adapted to receive said tufts therein.

9. An automatic cleaning device in accordance with claim 8, wherein said top and bottom bearing members define an access opening at one end communicating with said cavity and adapted to reciprocally receive said rack means therethrough.

10. An automatic cleaning device in accordance with claim 9, wherein said bottom bearing member includes a plurality of openings which are generally symmetrically oriented for rotatably receiving the receptacle portions of said drive and driven gears therethrough.

11. An automatic cleaning device in accordance with claim 10, wherein said rack means includes an elongated rack- member- having integral rack teeth on opposite sides thereof, said rack teeth extending normal to the longitudinal axis of said rack member and including at least one integral cam-like guide portion extending substantially along the length thereof, said cam-like guide portion adapted for camming and guiding co-action with a confronting interior surface defined by the access opening into said cavity and in one of said bearing members for maintaining alignment of said rack member during reciprocal driving movement thereof.

12. An automatic cleaning device in accordance with claim 11, wherein the drive gear portions of said drive gear have an axial width greater than the corresponding axial width of the driven gear portions of said drive gears with substantially only the upper one-half of said drive gear portions being engageable by said rack member, and with substantially the lower one-half portion engaging the associated driven gear portion of an adjacent driven gear, whereby successive driven gears are reciprocally, rotated and counter-rotated upon meshing inter-engagement of the associated driven gear portions.

13. An automatic cleaning device in accordance with claim 12, wherein said bearing members are made from a polymeric material, and said top bearing member having an enlarged boss-like area adjacent one end adapted to receive the relatively enlarged axial width of said drive gear portions therein.

14. An automatic cleaning device in accordance with claim 1, wherein the handle member includes a battery gear means attached to said output shaft in rotary engagement therewith, a face gear means engaging said pinion means a crank arm means pivotally and eccentrically attached at a first end to said face gear means, and a rack drive shaft means pivotally attached at a first end to a second end of said crank arm means, and connected to an end of said rack means at a second end of said rack drive shaft.

15. An automatic cleaning device in accordance with claim 14, including a control switch assembly disposed interiorly of said handle portion including a manual switch element for selectively energizing said battery-powered motor for translating rotational movement of said face gear means into reciprocal movement of said rack means for reciprocally, counter-rotating said tufts.

16. An automatic cleaning device in accordance with claim 1, wherein said rack means includes an elongated rack member disposed for reciprocal movement interiorly of said brush head portion, said rack member being coupled to a drive shaft, a bearing member fixedly attached to the interior of said brush head member and having an axial passageway for slidably receiving said drive shaft therethrough, and a flexible valve member carried by said bearing member and engageable with said drive shaft adapted to provide a one-way fluid seal relative to the interior of said brush head member.

17. An automatic cleaning device in accordance with claim 16, wherein said bearing member includes a body member having aperture means therein, said flexible valve member disposed adjacent one side of the bearing adapted for flexibly opening and closing said aperture means in response to fluid pressure alternately exerted upon said flapper valve member in response to reciprocal movement of said rack member whereby residue materials contained in said brush head member are expelled therefrom.

18. A cleaning device in the form of a motor driven toothbrush for cleaning surfaces and crevices of teeth comprising, a housing having a powered handle member and a brush head member, said brush head member including a hollow brush head portion adapted to receive top and bottom bearing members therein, said bearing members together defining a cavity therebetween, a driven gear means including a plurality of tuft holding, series driven gears disposed for reciprocal, rotation and counter-rotation upon driving engagement by at least one tuft holding drive gear, said tuft holding drive gear having a gear portion engageable with at least one gear of said driven gear means upon driving engagement of said tuft holding drive gear means by a rack member, said driven gear means being out of engagement with said rack means.

19. An automatic cleaning device in accordance with claim 18, wherein said tuft holding drive and driven gears each include a body member having a tuft receiving receptacle portion and an integral drive or driven gear portion, and the drive gear portion on said drive gear having a greater axial width as compared to the corresponding axial width of said driven gear portion of said driven gears so that said rack means substantially meshes only with the drive gear portions of said drive gear, and said driven gear portions drivingly mesh with one another.

20. An automatic cleaning device in accordance with claim 18, wherein said rack means includes an elongated rack member having a plurality of laterally spaced drive teeth disposed on opposed sides thereof, and said rack member including guide means disposed generally intermediate said drive teeth for guiding reciprocal movement of said rack member relative to said tuft holding drive gear.

21. An automatic cleaning device in accordance with claim 18, wherein said tuft holding drive and driven gears include drive and driven gear portions, the drive gear portions of said tuft holding drive gear being drivingly engaged by said rack means such that said tuft holding driven gears are reciprocally, rotated and counter-rotated by meshing engagement with the drive gear portions of the tuft holding drive gear while being substantially free of driving engagement with said rack means.

22. An automatic cleaning device in accordance with claim 21, wherein said tuft holding drive and driven gears each include a tuft holding receptacle portion and an integral drive or driven gear portion, said receptacle portion being adapted to detachably retain a tuft of filaments therein.

23. An automatic cleaning device in accordance with claim 18, wherein said tufts each comprise a bundle of polymeric filaments, said filaments in each tuft being fused together at one end to provide a generally solid mass-like body portion for detachable insertion into and out of the associated of said receptacle portions.

24. An automatic cleaning device in accordance with claim 23, wherein said tufts are disposed in at least two oppositely disposed rows on opposed sides of said rack means, the tufts in each of said rows being oriented in a generally staggered relationship relative to one another, and with adjacent tufts in each of said rows being longer and shorter in axial length relative to one another.

25. An automatic cleaning device in accordance with claim 18, including top and bottom bearing members defining a cavity therebetween adapted to receive said tuft holding drive gear and driven gears therein, said tuft holding drive and driven, gears each including integral drive and driven gear portions, respectively, and integral tuft holding receptacle portions, said drive and driven gear members being rotatably journaled at one end in said top bearing member with said receptacle portions extending through said bottom bearing member and communicating with the exterior of said bottom bearing member and adapted to receive said tufts therein.

26. An automatic cleaning device in accordance with claim 25, wherein said top and bottom bearing members define an access opening at one end communicating with said cavity and adapted to reciprocally receive said rack means therethrough.

27. An automatic cleaning device in accordance with claim 25, wherein said bottom bearing member includes a plurality of openings which are generally symmetrically oriented for rotatably receiving the receptacle portions of said drive and driven gears therethrough.

28. An automatic cleaning device in accordance with claim 25, wherein said rack means includes an elongated rack member having integral rack teeth on a portion of opposite sides thereof, said rack teeth extending normal to the longitudinal axis of said rack member and including at least one integral cam-like guide portion extending substantially along the length thereof, said cam-like guide portion adapted for camming and guiding coaction with the confronting interior surface defined by the access opening into said cavity and one of said bearing members for maintaining alignment of said rack member during reciprocal driving movement thereof.

29. An automatic cleaning device in accordance with claim 19, wherein the drive gear portions of said drive gear has an axial width greater than the corresponding axial width of the driven gear portions of said driven gears with substantially only an upper one-half of said drive gear portion being engageable by said rack member, and with substantially a lower one-half portion engaging the associated driven gear portion of an adjacent driven gear whereby successive driven gears are reciprocally, rotated and counter-rotated upon meshing engagement with driven gear portions of associated driven gears.

30. An automatic cleaning device in accordance with claim 29, wherein said bearing members are made from a polymeric material, and said top bearing member having an enlarged boss-like area adjacent one end adapted to receive a relatively enlarged axial width of said drive gear portion therein.

31. An automatic cleaning device in accordance with claim 18, wherein the handle member includes a battery-powered motor having a rotatable output shaft, a pinion means attached to said output shaft in rotary engagement therewith, a face gear means engaging said pinion means, a crank arm means pivotally and eccentrically attached at a first end to said face gear means, and a rack drive shaft means pivotally attached at a first end to a second end of said crank arm means, and connected to an end of said rack means at a second end of said rack drive shaft means.

32. An automatic cleaning device in accordance with claim 31, including a control switch assembly disposed interiorly of said handle portion including a manual switch element for selectively energizing said battery-powered source for translating rotational movement of said face gear means into reciprocal movement of said rack means for reciprocally counter-rotating said tufts.

33. An automatic cleaning device in accordance with claim 18, wherein said rack means includes an elongated rack member disposed for reciprocal movement interiorly of said brush head member, said rack member being coupled to said drive shaft, a bearing member fixedly attached to the interior of said brush head member and having an axial passageway for slidably receiving said drive shaft therethrough, and a flexible valve member carried by said drive shaft and engageable with said bearing member adapted to provide a one-way fluid seal relative to the interior of said handle member.

34. An automatic cleaning device in accordance with claim 33, wherein said bearing member includes a body member having aperture means therein, said flexible valve seal member disposed adjacent one side of the bearing member adapted for flexibly opening and closing said aperture means in response to fluid pressure alternately exerted upon said flapper valve seal member in response to reciprocal movement to said rack member, whereby residue materials contained in said brush head member are automatically expelled therefrom.

35. A cleaning device of the type including a motor drive brush unit comprising at least one tuft holding drive gear member operatively connected to one of a plurality of series interconnected tuft holding driven gear members, a rack means disposed for driving said tuft holding drive gear member, such that said drive and driven gear members are concurrently reciprocally rotated and counter-rotated by said rack means, said rack means engaging only said drive gear and being out of engagement with said driven gear members.

36. A cleaning device in accordance with claim 35, wherein said tuft holding drive gear member includes a drive gear portion and a receptacle portion for mounting a tuft therein, and said rack means engaging said drive gear portion of said drive gear member and being free of engagement with gear portions of said driven gear members.

37. A cleaning device in accordance with claim 36, wherein each of said tufts is comprised of a plurality of polymeric filaments heat fused together at one end to provide a generally solid mass-like base adapted to be detachable mounted within the receptacle portion of the drive and driven gear members.

* * * * *